United States Patent
West

(10) Patent No.: US 6,594,835 B2
(45) Date of Patent: Jul. 22, 2003

(54) IMPACT CUSHIONING SYSTEM SENSOR TO DETECT AND PREVENT FALL RELATED INJURIES

(76) Inventor: Raymond O. West, P.O. Box 1137, Belfair, WA (US) 98528

( * ) Notice: Subject to any disclaimer, the term of this patent is extended or adjusted under 35 U.S.C. 154(b) by 0 days.

(21) Appl. No.: 09/972,432

(22) Filed: Oct. 5, 2001

(65) Prior Publication Data

US 2003/0066131 A1 Apr. 10, 2003

(51) Int. Cl.[7] .......... A47C 21/08; A47C 27/08; B60R 21/16
(52) U.S. Cl. .......... 5/424; 182/137; 5/940
(58) Field of Search .......... 5/424, 600, 658, 5/93.1, 420, 706, 940; 182/137

(56) References Cited

U.S. PATENT DOCUMENTS

| | | | |
|---|---|---|---|
| 5,052,065 A | 10/1991 | West | 5/424 |
| 5,592,705 A | 1/1997 | West | 5/424 |
| 6,314,596 B1 * | 11/2001 | Neff | 5/420 |
| 6,386,576 B1 * | 5/2002 | Kamen et al. | 280/728.1 |
| 2002/0144345 A1 * | 10/2002 | Lane | 5/424 |

* cited by examiner

Primary Examiner—Alexander Grosz
(74) Attorney, Agent, or Firm—Richard C. Conover

(57) ABSTRACT

This invention relates to an impact-cushioning device, which is designed to prevent injury when an occupant, confused or otherwise, falls from a height. This may be a bed or bunk, gurney or examination table. The device generally comprises an impact-reducing cushion. This cushion may be air filled or of a variety of impact absorbing materials. Also provided is a means of displacing the cushion to intercept the falling individual before he or she strikes the floor. The departure of the individual from the bed is detected by signals that are generated when one or more edge pressure switches are actuated simultaneously with signals from one or more light beam sensors. Signals thus generated are processed through an electronics module and passed to a solenoid valve. When the valve opens, gas from a canister is passed to a telescoping device. This in turn displaces the cushion. Thus a protective barrier is placed between the bed occupant and the floor.

5 Claims, 3 Drawing Sheets

IMPACT CUSHIONING SYSTEM SENSOR TO DETECT AND PREVENT FALL RELATED INJURIES

CROSS REFERENCE TO RELATED APPLICATION

This application is related to application Ser. No. 394,447, Filed Feb. 27, 1995, now U.S. Pat. No. 5,592,705, granted Jan 14, 1997.

FIELD OF INVENTION

This invention relates in general to safety equipment designed to prevent injury from falls and more particularly to a sensing device designed to trigger displacement of a cushioning device that protects bed-occupants, or the like, from fall-related injuries.

BACKGROUND—DESCRIPTION OF PRIOR ART

Physicians and nurses, indeed all persons who care for the elderly and the confused, are aware of the trauma and its consequences related to falls; especially to falls from beds. Trauma happens in hospitals, convalescent hospitals, assisted care facilities, even in private homes where care is given to the frail-elderly and or confused for whatever reason. Trauma often involves fractured bones including hips, skulls, ribs among others. Morbidity is often severe leading to death or prolonged convalescence. The cost to society is substantial.

Falls from bed are frequently associated with periods of confusion during which the patient deliberately attempts to exit the bed even when it requires climbing over side rails. Confusion is often dealt with by restraining the patient, either with fabric restraints or medicines. Neither of these preventive methods is satisfactory. Federal and State health-related agencies, facility caregivers, patients and their families decry the necessity to employ restraints for safety. Furthermore, these preventive measures are incapable of protecting the patient after the fall has begun. A cushioning device that inserts itself between the patient and the floor is necessary if morbidity and mortality is to be averted.

The economic cost of falls from bed is enormous. Billions of scarce healthcare dollars may be spared and utilized for other needy purposes if we can prevent injuries of this nature. And we can.

U.S. Pat. No. 5,052,065 to West, 1992 discloses a means whereby a cushioning air bag is filled with gas stored under pressure in a canister. Using current technology, the extreme cost of this embodiment prohibits its use. Thus it is not feasible for current preventive care.

U.S. Pat. No. 5,592,705 to West, 1997 discloses a means whereby a cushioning device is displaced from beneath or beside a bed. It inserts itself between the falling patient and the floor. Bellows or piston or other telescoping devices, which are energized by stored gas, displace the cushion. The gas is delivered through a valve that is actuated by electrical current. This electrical signal is in turn actuated by a prior electrical signal that is generated from pressure sensitive switches. These are disposed in the mattress of the bed. The signal is generated when the patient leaves the bed thus triggering the pressure switches.

SUMMARY OF THE INVENTION

A superior means for sensing the risk of patient fall is found in a new sensing embodiment. Herein is employed a plurality of sensors. The first is one or more pressure sensitive edge sensors. These are disposed on bedside rails or bed frame or both. The second is one or more light sensitive sensors. These are disposed on or near the bed. They are positioned so that an individual at risk cannot leave the bed without interrupting a beam of light. The system deploys when these sensors are simultaneously activated.

According to the embodiment of the prior art there is provided an impact cushion device for the prevention of injury to a bed occupant who leaves the bed and falls to the floor. A prior patent describes the mechanism of cushion displacement. On Jan. 14, 1997 R. O. West was issued a U.S. Pat. No. 5,592,705 relating to an impact cushioning device to prevent or alleviate injury due to falls from beds or other objects, both in acute hospitals, convalescent hospitals, indeed in any venue where the sick or disabled are domiciled and require care. The embodiment also provides means for the safety of infants and toddlers who may require protection from falls from any height or object.

The device of U.S. Pat. No. 5,592,705 depends on a pressure mattress and plural sensitive switches to initiate the deployment of a protective cushion. This deployment is accomplished so quickly that the cushion interposes itself between the falling patient and the floor. Thus it cushions the impact and prevents or alleviates injury.

The cushion portion of the invention generally comprises an inflatable air cushion or a plurality of other impact absorbing materials. The cushioning portion is oriented by a plurality of positions to the bed, or other object of patient harborage, in such a manner wherein the cushion upon displacement creates a barrier between the bed occupant and the floor, when displaced. At least one cushioning portion is stowed relative to the frame portion of the bed.

The displacement means of U.S. Pat. No. 5,592,705 issued to West comprises a canister containing a supply of stored gas.

This canister is fluidly connected to a valve mechanism disposed between the canister and one or more telescoping means. These telescoping means are in turn attached to a cushion portion. The telescoping portion of the invention is disposed to said cushion portion such that when the gas is released the telescoping means displaces the cushion portion. The cushion inserts itself between the floor and the falling individual. The valve portion is normaly closed. Upon signal the valve opens releasing the stored gas. This is the preferred embodiment, but not the only one. Potential energy for cushion displacement includes spring loading and stretchable elastic means.

This patent application describes an alternate means to provoke a signal to the displacement means.

A light sensing means is mounted on one or both sides of the bed with light beam emitted constantly from one longitudinal extremity of the bed to the other. The light may be of a plurality of beams that can be sensed from the foot of the bed to the top of the bed or the upper end of the bed to the foot thereof. The source of light beam and the sensor of the beam may be mounted in any fashion or position that upon interruption will sense any object from any position that interrupts it.

When the system is turned on, the beam-sensing portion constantly discerns the beam. When the beam is interrupted, as by a person seeking exit from the bed, an electrical impulse flows to the valve mechanism electrically connected to the beam-sensing portion.

The system remains inert until signals are received from one or a plurality of edge switches mounted on the upper surface of bed siderails. Added to this is one or a plurality of proximity sensors, which are positioned, superior to the bedrail. Signals from both the edge switch and the proximity switch must be simultaneously present for the valve to release the burst of stored gas from the canister. Only then the cushion is deployed.

One or more proximity sensor means are mounted on or near the bed. This is means to sense the approach of another person whether an attendant or a visitor. This sensor means inactivates the system thus shutting it down.

This invention provides a unique sensing means that triggers the displacement of the cushion.

A switch means is also provided for selectively activating and deactivating the sensing means.

It is therefore an object of this present invention to provide a sensing device designed to actuate an impact cushioning device for protecting individuals from injuries that occur during falls from beds or other elevated objects.

Another object of the present invention is to provide a superior embodiment of expansion devices that provide means for cushion deployment.

Another object of the present invention is to provide one or more proximity sensors designed to inactivate the entire system when individuals other than the individual at risk is present in the immediate environment.

BRIEF DESCRIPTION OF THE DRAWINGS

These and other features of the present invention will become apparent upon reference to FIGS. 1, 2, and 3.

Figure 1:
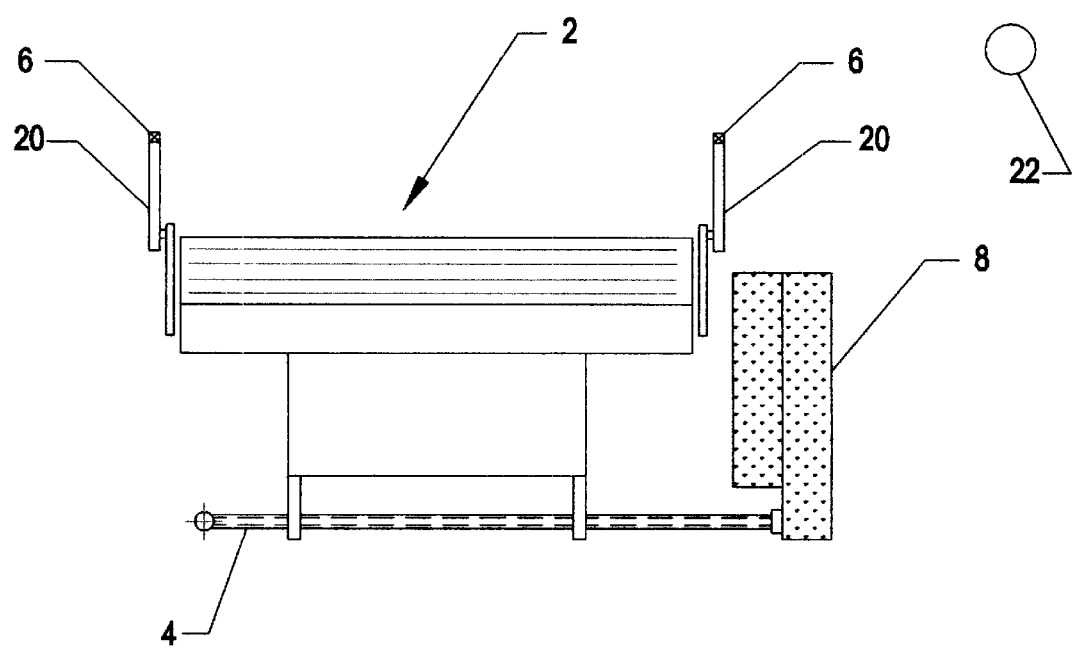
FIG. 1. Is an end view of a bed 2 and illustrates the embodiment of displacement means 4 in a non-deployed state, and a sensing edge switch 6 attached to a side rail 20. Also this view incorporates an impact cushioning portion 8 stowed beside the bed, poised for instant displacement. Also this view shows a remote motion sensing device 22 mounted strategically and remotely to detect movement in the immediate vicinity of the bed and its occupant. Said sensor inactivates the entire system when motion is detected.

Herewith we have described a means of sensing an unexpected departure of an occupant from bed or other resting venues including gurneys, and examining tables, and a means of interposing a cushioning portion between the patient and the unforgiving floor. Injury is thus prevented or minimized.

REFERENCE NUMERALS USED IN DRAWINGS:

Bed frame---2
Displacement means---4
Sensing Edge Switch---6
Cushion Portion---8
Fixed Field Proximity Sensor--10
Electronics Module---12
Canister for Stored Gas---14
Solonoid Valve---16
Hose Connecting Means---18
Side Rails---20
Remote Motion Sensing Device---22

DETAILED DESCRIPTION OF THE PREFERRED EMBODIMENT

Referring now to the drawings wherein the figures shown are for the purpose of illustrating preferred embodiments of the present invention and not for the purpose of limiting the same.

FIG. 1 illustrates a bed 2 constructed in accordance with a first embodiment of the present invention. Bed 2 generally comprises a frame portion, head and foot ends and mattress.

Fluidly connected to valve mechanism 16 is a replaceable canister 14 containing therein a supply of compressed gas. Valve mechanism 16 is also electrically connected to at least one pressure sensitive edge switch 6 and at least one fixed field proximity sensor 10. The valve mechanism is normally closed whereby the compressed gas is retained within canister 14. When operable in the open position the compressed gas is free to flow from canister 14 into connection line 18 and thence to propulsion portion 4. When propulsion portion 4 is filled with gas from canister 14 the impact-cushioning portion 8 is displaced in a means to intervene between a falling individual and the floor. In this regard the signals generated from sensing edge switch 6 and fixed field proximity sensor 10 are operable to actuate valve mechanism 16 from its normally closed to its open position. Though not shown, bed 2, or its immediate enviroment, further includes an on/off switch which is movable between an on and an off position for selectively activating and deactivating the entire system. Though also not shown it is further contemplated that the electronics module 12 will include an audible or visual alarm electronically connected thereto. In this regard, the alarm is activated when valve mechanism 16 actuates to an open position, thereby informing attending personnel that the occupant has departed from the bed, gurney or examining table.

Though also not shown in detail the system also incorporates a remote motion sensing device mounted remotely but in the general area of the bed occupant. Said motion sensor detects movement other than that of the bed occupant and inactivates the entire system. The motion sensor thereby obviates any possible injury to an individual moving toward the bed occupant simultaneously with impact cushion deployment.

Figure 2:
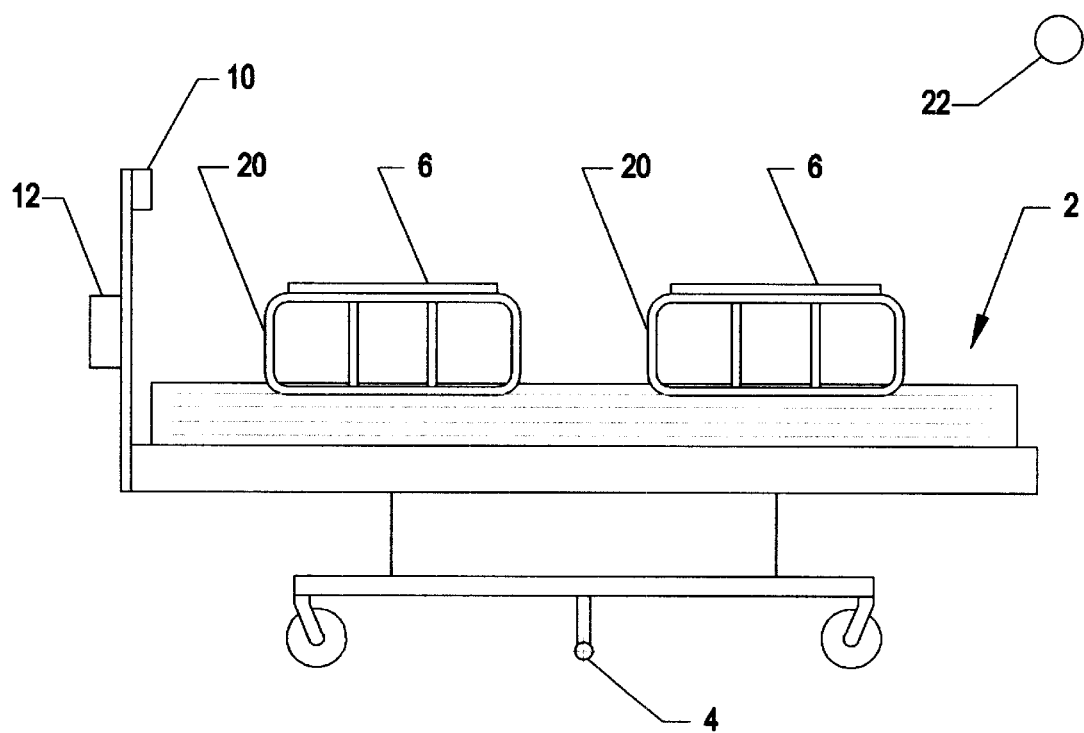
FIG. 2 is a side view of a bed 2 illustrating the manner in which sensing edge switch 6 is mounted on side rails 20. The propulsion portion 4 is viewed on end. A fixed field proximity sensor 10 is viewed as mounted on one end of the bed. An electronics module 12 is viewed as mounted in this embodiment on an end of the bed. Also this view shows a remote motion sensor as described in FIG. 1.
Figure 3:
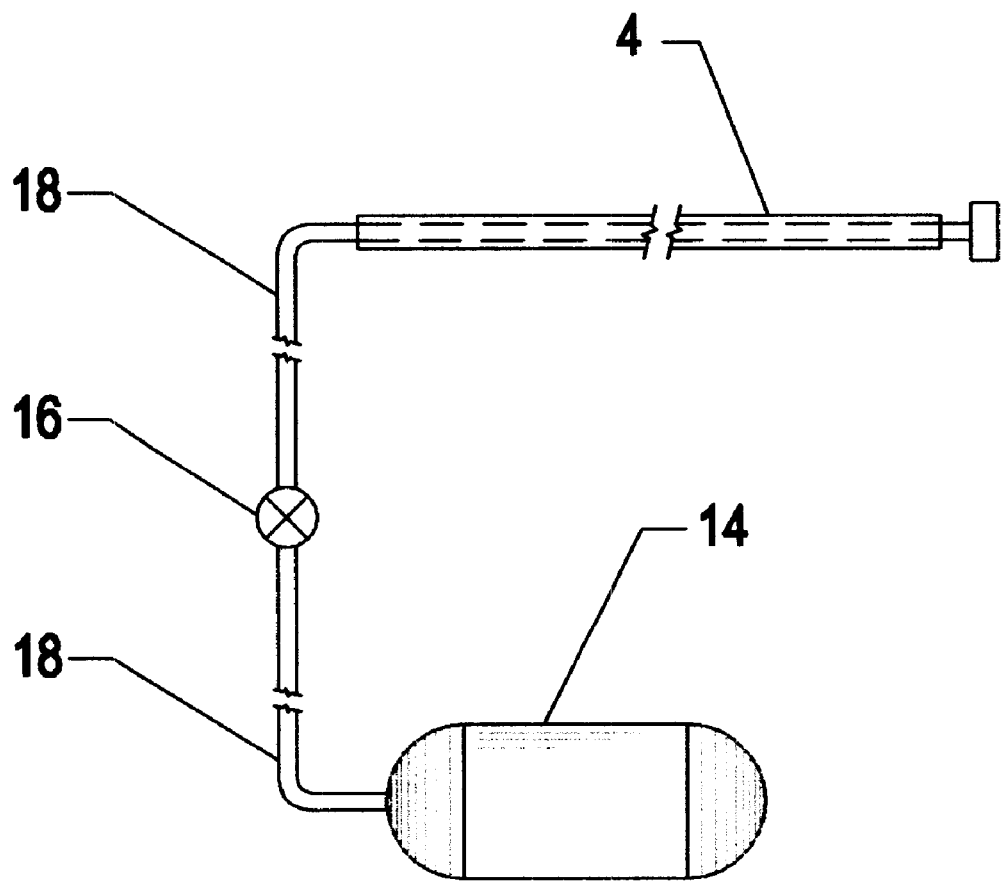
FIG. 3 views propulsion portion from above and illustrates a canister for stored gas 14, a solenoid valve 16 interposed and connected by means of hose 18 to displacement means 4 which may be of a plurality of means including but not limited to telescoping tubing, bellows and other expansion portions.

Though not specifically illustrated in the present FIGS. 1, 2, and 3 it is immediately evident that the present sensor means described is at once compatible with the means disclosed in U.S. Pat. No. 5,592,705 to West 1992. Therein, a bed is constructed or modified to include an impact cushioning device stowed and displaced in a plurality of embodiments.

Both sides of the bed, gurney or examining table can be thus rigged and protected. In practice the bed, gurney or examination table can be placed against a wall of the room occupied by said individual. Thus it is generally necessary to protect only one side of bed, gurney or examination table. In this connection it will be appreciated that injury from falls from the foot of the bed, gurney or examination table can be prevented by means of a similar embodiment of canister, solenoid release valve, connecting line, bellows or other telescoping portions and impact cushioning portion.

Though the present invention has been described as being utilized in conjunction with the patient's bed or a gurney or an examination table it will be appreciated that the present invention may incorporate additional modifications and improvements to protect against falls from wheelchairs, toilets as well as ambulation related therapy applications.

The particular combination of parts described and illustrated herein is intended to represent the preferred embodiment of the invention and is not intended to serve as limitations of alternate devices within the spirit and scope of the present invention.

What is claimed:

1. Impact cushioning device for protecting a bed occupant from fall-related injuries comprising:

a bed (2) having a frame portion, side rails (20) and a horizontal mattress portion;

at least one pressure sensing means having a pressure switch (6) disposed on or about a side rail, said pressure sensing means being operable to generate a first signal when said occupant applies pressure to the pressure switch (61);

at least one light generating means for generating a beam of light which extends above a side rail (20) from one longitudinal extension of the bed (2) to the other;

at least one light beam sensing means (10) disposed on or about the frame portion and aligned to receive the beam of light, the light beam sensing means (10) being operable to generate a second signal when the occupant interrupts the beam of light;

an electronics module means (12) for sensing and processing the first and second signals and for transmitting a third signal when either the first signal or the second signal is sensed;

a cushion portion (8) stowed in relationship to the frame portion;

a gas actuatable telescoping means (4) attached to the cushion portion (8), the telescoping means (4) disposed to displace the cushion portion (8);

inflating means fluidly connected to the telescoping means (4) for providing gas under pressure to the telescoping means (4) to actuate the telescoping means (4); and a solenoid valve means (16) electrically connected to the electronics module means (12), the solenoid valve operable from a normally closed position to an open position to permit the flow of gas from the inflating means (14) to the telescoping means (4) when the third signal is received from the electronics module means (12).

2. The device of claim 1 wherein the inflating means includes a canister (14) containing a supply of compressed gas, said canister being fluidly connected to the solenoid valve means (16).

3. The device of claim 1 wherein an alarm is electrically connected to the solenoid valve and is activated when the solenoid valve is in an open position.

4. The device of claim 1 wherein the cushion portion comprises a cushion adapted to displace outwardly from at least one longitudinally extending edge of said bed.

5. The device of claim 1 further including a switch means for selectively activating and deactivating the pressure sensing means and the light beam sensing means (10), and a motion sensing device (22) for detecting remote movement, said motion sensing device electrically connected to the switch means to deactivate the pressure sensing means and the light beam sensing means when motion is detected.

* * * * *